(12) United States Patent
Cruz

(10) Patent No.: US 6,540,710 B1
(45) Date of Patent: Apr. 1, 2003

(54) NON-COMPRESSION WRIST BRACE

(76) Inventor: Mark Cruz, 444 Brown Trail, Hopatcong, NJ (US) 07843

( * ) Notice: Subject to any disclaimer, the term of this patent is extended or adjusted under 35 U.S.C. 154(b) by 0 days.

(21) Appl. No.: 09/550,985

(22) Filed: Apr. 17, 2000

Related U.S. Application Data

(60) Provisional application No. 60/131,503, filed on Apr. 29, 1999.

(51) Int. Cl.[7] .................................................. A61F 5/00
(52) U.S. Cl. ........................................ 602/21; 128/878
(58) Field of Search ............................ 602/20, 21, 22; 128/869, 877, 878, 879, 882

(56) References Cited

U.S. PATENT DOCUMENTS

| | | | | |
|---|---|---|---|---|
| 4,782,825 A | * | 11/1988 | Lonardo | 602/21 |
| 4,960,114 A | * | 10/1990 | Dale | 602/21 |
| 4,977,890 A | * | 12/1990 | Mann | 602/21 |
| 5,020,515 A | * | 6/1991 | Mann | 602/21 |
| 5,205,812 A | * | 4/1993 | Wasserman | 128/878 |

* cited by examiner

*Primary Examiner*—Michael A. Brown
(74) *Attorney, Agent, or Firm*—Bernard Murphy

(57) ABSTRACT

The novel wrist brace is designed to fixedly link a users hand to a users forearm in a rigid fashion whereby the wrist is held in a relatively neutral position. It is a further intent of this invention to do so without applying pressure to the volar surface of the forearm or to the carpal tunnel area of the wrist.

7 Claims, 4 Drawing Sheets

NON-COMPRESSION WRIST BRACE

This application claims the benefit of Provisional Application No. 60/131,503 filed Apr. 29, 1999.

OBJECTS OF THE INVENTION

It is an object of my invention to set forth an improved wrist brace that does not compressively engage the volar surface of the wrist and, rather it bridges across the wrist, between the hand and forearm, to both isolate and immobilize the wrist.

It is particularly an object of the invention to disclose a non-compression wrist brace comprising a body; said body having a longitudinal limb, with an open cuff at one end of said limb, and a transverse element at the opposite end of said limb. Said cuff comprises means for girding only the dorsal side, and the lateral flanks, of a forearm; said element comprises means for engaging the dorsal side of a hand; said cuff has a cincture joined thereto for clasping said cuff fast to such a forearm. Said element has a cincture joined thereto for clasping said element fast to the dorsal side of such a hand wherein said cuff and said element cooperatively define means for non-contactingly bridging across a wrist, between such forearm and such hand, with said limb, to isolate said wrist and immobilizing such wrist; and said limb is unyieldably rigid.

It is a further object of this invention to set forth a non compression wrist brace comprising a body; said body having (a) a limb, (b) means for girding only the dorsal side, and the lateral flanks of a forearm, and (c) means for engaging the dorsal side of a hand; and including only one pair of cinctures for clasping said girding means and said engaging means fast to such forearm and such hand, respectively; wherein said engaging means and said girding means cooperatively with said limb, define means for non-contactingly bridging across a wrist, between such forearm and such hand, to isolate said wrist and immobilizing the latter; and said limb is unyieldably rigid.

DESCRIPTION OF PRIOR ART

All current wrist brace technology that focuses solely on holding the wrist in a neutral position compresses the volar surface and the flexor tendons in some means. The compression is either through the brace itself like Reese's invention, patent #5,279,545, Goulds invention, patent #5,766,141, Eck's invention, patent #5,746,707, or through the placement and fastening means designed to hold the brace in place such as Working's Carpal Brace invention, patent #4,941,460. As an example, while Working states the brace can hold the wrist in the neutral position, and that the straps surround the middle and upper portions of the forearm, this is not entirely true. First, the straps do not surround the middle and upper portions of the forearm, they surround the lower and middle sections of the forearm. If they surrounded the middle and upper portions of the forearm the brace would not work well. The wrist would be unsupported and too loosely held to restrict movement. Working's brace is sold under the name Carpallock®. Measurements of a properly sized brace show the brace overall is eight inches in length. The distance of an average user's forearm as measured from the top of the hand just behind the knuckles (where the front of Working's brace is fastened) to the elbow is fourteen inches. The distance of the first forearm strap of the Carpallock®, measured back from the front edge of the brace, is four inches. This places the strap just behind the distal end of the ulna, clearly surrounding the lower end of the forearm and applying pressure to the volar surface wherein lie the flexor tendons and median nerve. Further, the elastic straps must be fastened very tightly to hold the brace in place since it only comprises a straight flat rigid piece affixed to the dorsal surface of the forearm. Any brace that requires circumferential pressure of an exposed elastic strap will undoubtedly compress the volar surface, applying pressure to the flexor tendons and median nerve.

There is a need for a lightweight, unobtrusive, simple splint to hold the wrist in a neutral position while at the same time not compressing the volar surface wherein lies the flexor tendons and median nerve. My new invention accomplishes this.

SUMMARY OF THE INVENTION

The invention is a splint designed to hold the wrist in the neutral position and block wrist movement in flexion, extension and ulnar/radial deviations. The brace is specifically designed for the treatment of carpal tunnel syndrome and secondarily is designed to be used as a general purpose static splint.

Carpal tunnel syndrome or CTS is caused from the inflammation of the flexor tendons applying pressure to the median nerve. These tendons and nerve are in the volar surface of the forearm and pass through the transverse carpal ligament and the carpal bones. The transverse carpal ligament and the carpal bones form a tube called the "carpal tunnel". This carpal tunnel is located just where the hand meets the forearm just behind the palm however the tendons and nerve run up the forearm in the volar surface. These tendons become swollen and inflamed from over use and cause friction from rubbing against each other and from passing through the restriction of the carpal tunnel resulting in pressure to the median nerve. Tingling, numbness and pain are the result. The remedy is anti inflammatory drugs and immobilization. In extreme cases surgery is performed to cut the transverse carpal ligament to enlarge the carpal tunnel. Regardless, for recovery it is important to hold the wrist in a neutral position and limit the hands movement all the while not compressing the volar surface and the carpal tunnel.

My brace is a one piece molded plastic unit lined with foam and held in place with only two releasable straps. One strap surrounds the hand piece and the second strap surrounds the forearm piece. The molding of the forearm piece is such that it grips the forearm from the sides and does not apply pressure to the underside of the forearm. The forearm strap flexes the side pieces rather than applying circumferential pressure directly to the forearm when tightened. The entire brace including straps weighs approximately 1.5 oz. This light weight is also a key accomplishment resulting from the simple design and use of lightweight plastics such as ABS or Kydex making the brace very appealing for long term usage such as at night. Research shows immobilizing the wrist overnight is an effective treatment. Further objects of this invention, as well as the novel features thereof will become evident by reference to the following detailed description of the invention, in conjunction with accompanying figures, in which:

BRIEF DESCRIPTION OF THE PICTURES

DETAILED DESCRIPTION OF THE INVENTION

Figure 1:
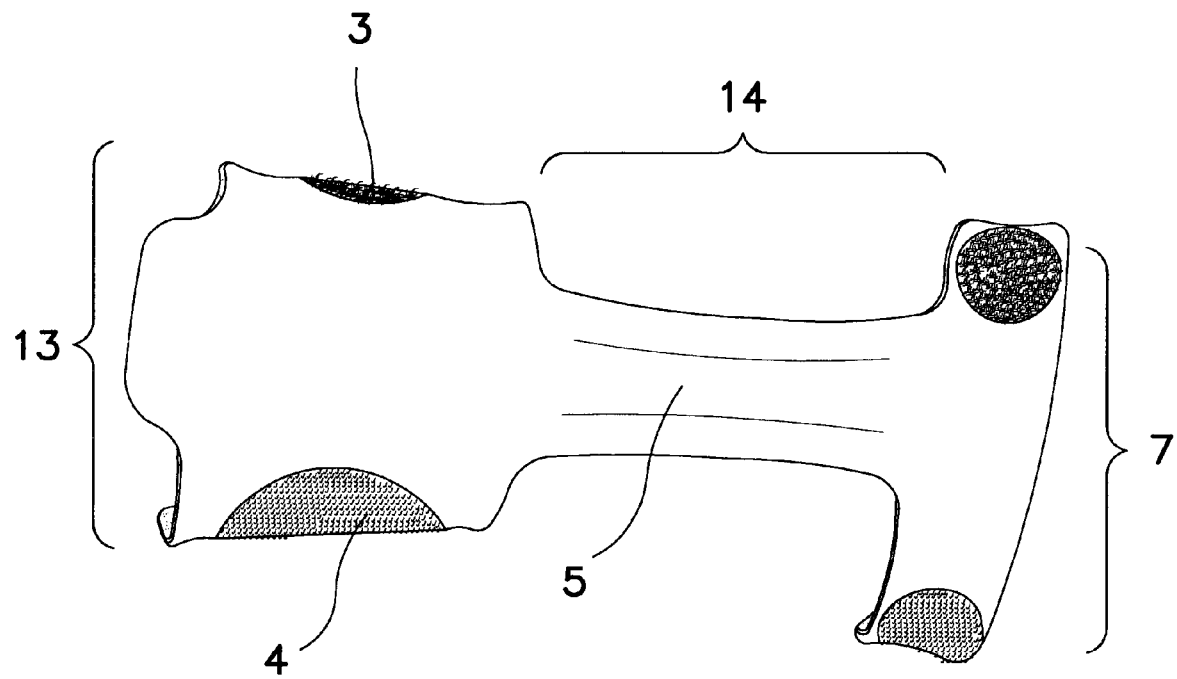
FIG. 1 is a top view of the wrist brace, without straps.
Figure 2:
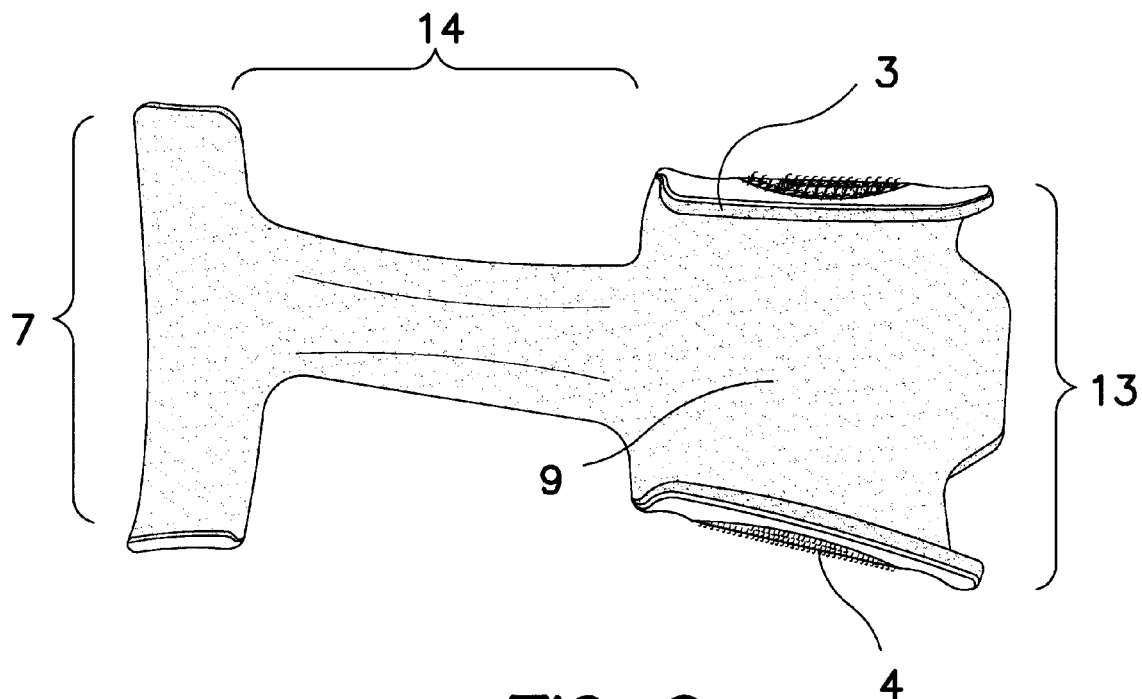
FIG. 2 is a bottom view of the wrist brace, without straps.
Figure 3:
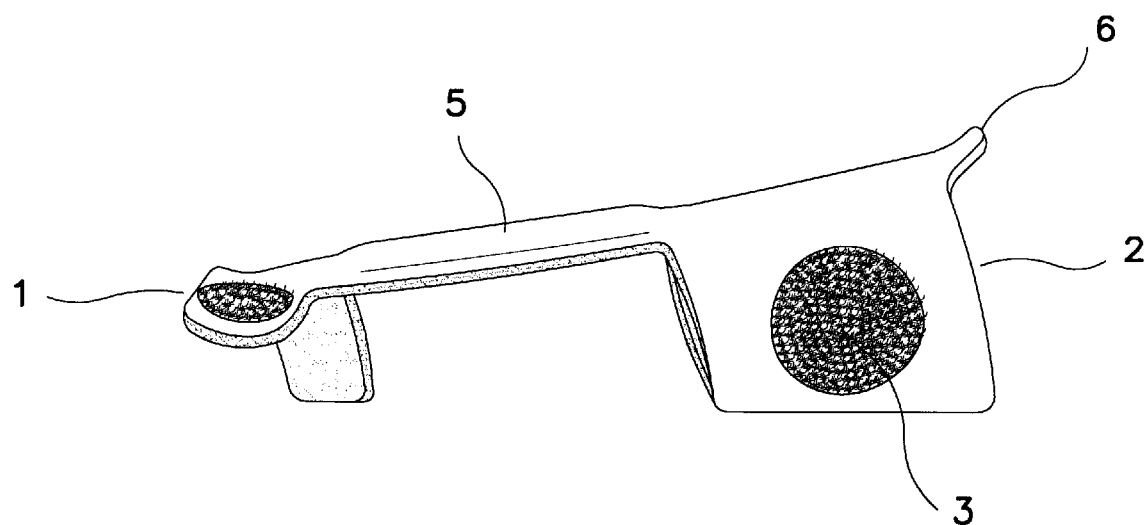
FIG. 3 is a left side view of a right-handed wrist brace, without straps.
Figure 4:
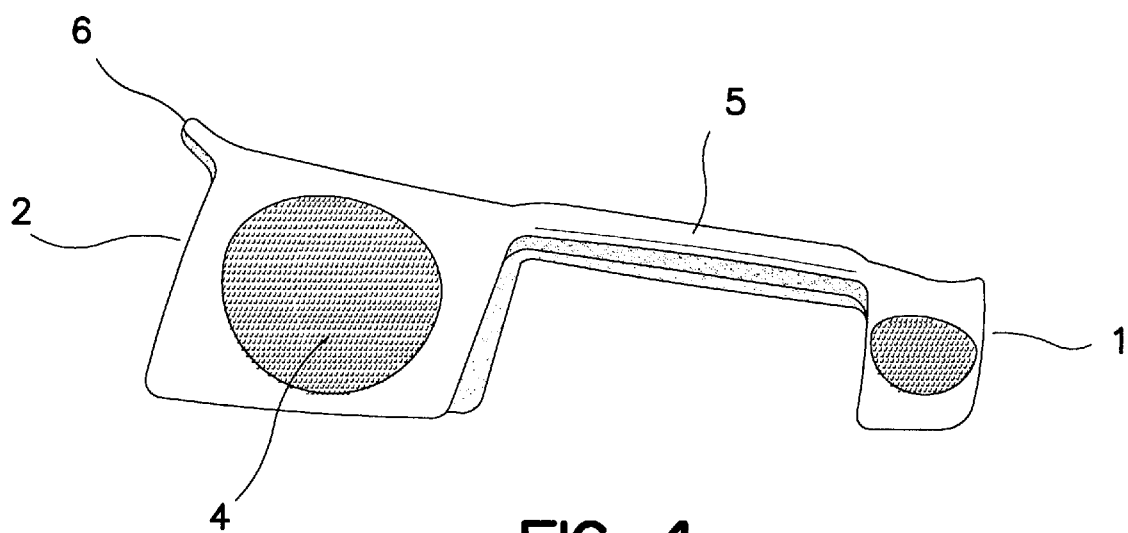
FIG. 4 is a right side view of a right-handed wrist brace, without straps.
Figure 5:
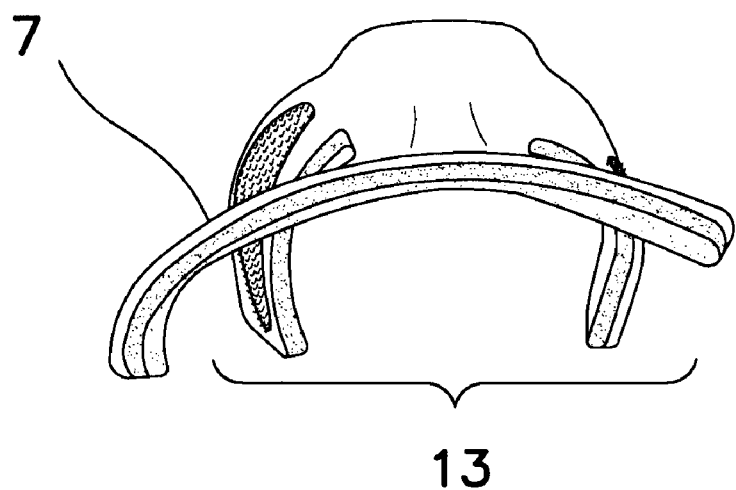
FIG. 5 is a front view of the wrist brace, without straps.
Figure 6:
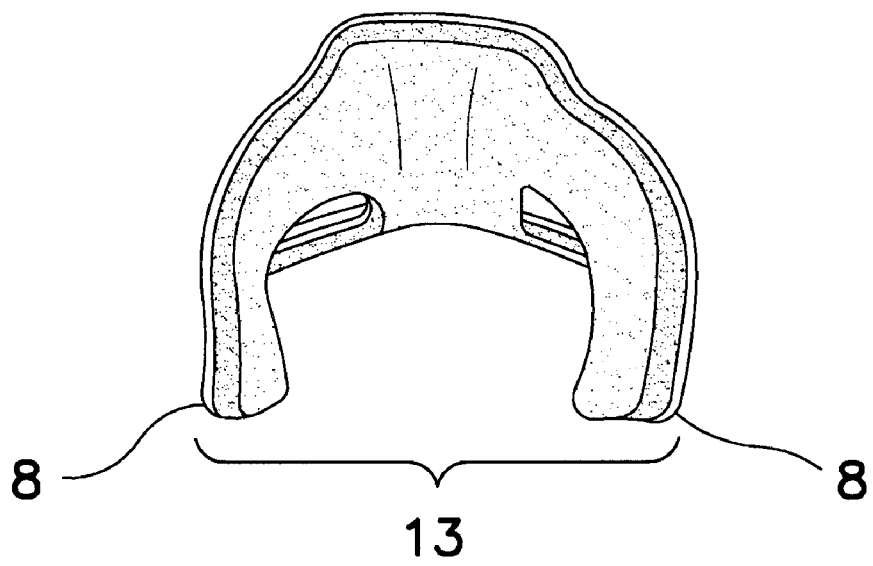
FIG. 6 is a rear view of the wrist brace, without straps.
Figure 7:
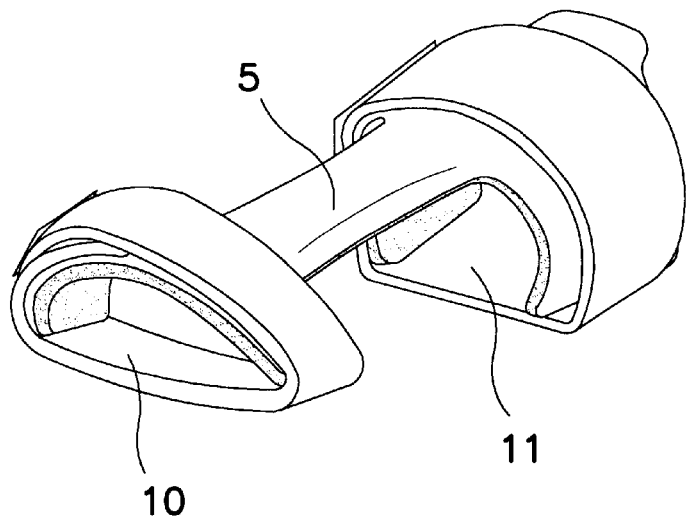
FIG. 7 is a three-quarter view of the wrist brace including fastening straps.
Figure 8:
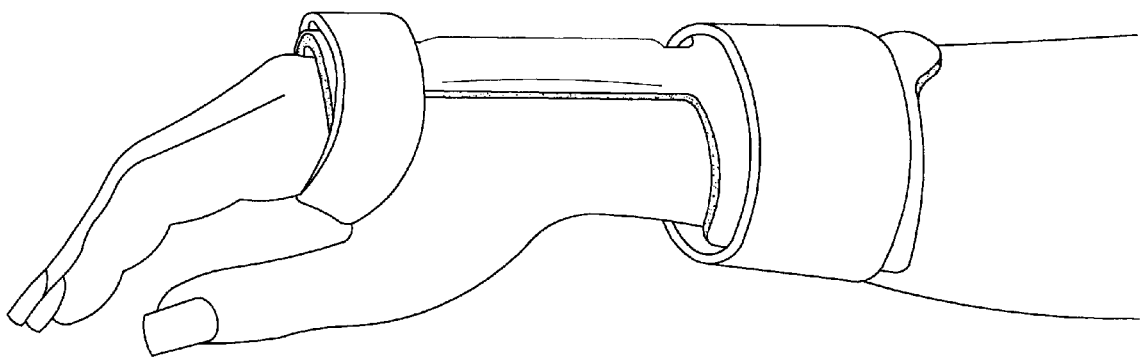
FIG. 8 is a three-quarter side view of the wrist brace as worn by a user.

As shown in FIGS. 1–8, the brace is a one-piece molded plastic unit designed to fit on the top or dorsal surface of the hand and forearm. The unit is lined with foam 9. As shown in FIGS. 2, 5, and 6 the brace has a "C"-shaped cuff 13 that partially wraps the users forearm. Picture the letter "C" rotated 90 degrees clockwise so the open portion of the "C" faces down, i.e. faces the under side or volar surface of the forearm. The "C" cuff 13 fits the forearm on the dorsal surface several inches behind the distal end of the ulna. There is a rigid limb 14 that extends from this "C" cuff 13 to the dorsal surface of the hand. This limb is narrow, approximately one inch in width and has a molded spine-like ridge or raised rib 5 in it running from the distal end 1 to the proximal end 2 of the brace. This ridge gives the limb 14 rigidity. At the proximal end 2 of the brace there is a flared tab component 6. At the distal end 1 of this limb 14 is a roughly perpendicular or transverse element 7 that spans the top or dorsal side of the hand just behind the knuckles; this comprises the handpiece at the distal end of the brace 1. This element 7 partially curves around the ulnar edge of the hand. The brace is affixed to the dorsal side of the forearm and hand as seen in FIG. 8. It is held in place with only two cinctures or straps. Encompassing both the handpiece element 7 and forearm cuff 13 are straps 10 and 11. The straps are coupled to the brace and close upon themselves with Velcro® fasteners. One handpiece strap 10 surrounds the front handpiece element 7, and the second proximal strap 11 surrounds the rear cuff 13 of the brace.

The molding of the brace is specific to its function. The rear cuff 13 that holds the forearm is described as a "C" cuff. As shown in FIGS. 2 and 6, this cuff 13 is molded to grasp the forearm laterally with its side walls 3 and 4, applying no pressure to the volar surface wherein lie the median nerve, the flexor tendons and the carpal tunnel. In fact, the gripping pressure is only applied to the ulna and radius bones leaving the open section of the "C" on the underside or volar surface of the forearm. When strap 11 is tightened, this "C" cuff 13 flexes on the dorsal surface in line with the ridge 5, allowing both side components 3 and 4 of the "C" cuff 13 to stay rigid and to close in on the sides of the forearm when the strap is tightened. This effects lateral compression to the forearm only. Further, the ends of the "C" cuff 13 are flared 8. These flares and the flexing of the side's keep the strap 11 from applying pressure to the exposed volar surface. It is this unique flexion of the "C" cuff 13 that holds the brace firmly yet does not compress the volar surface of the forearm.

Finally the brace is rigid enough to hold the hand firmly and to restrict its movement; however it is designed to deflect under significant force. For instance, if the user were in an auto accident, while wearing the brace, it would deflect as not to cause injury to the bones of the hand.

While I have described my invention in connection with a specific embodiment thereof, it is to be clearly understood that this is done only by way of example, and not as a limitation to the scope of my invention or the ambit of the claims.

I claim:

1. A non-compression wrist brace, comprising:

a body;

said body having longitudinal limb, with a open cuff, at one end of said limb, and a transverse element at the opposite end of said limb; wherein said cuff comprises first means or engaging the dorsal side, and the lateral flanks, of a forearm;

said element comprises second means for engaging the dorsal side of a hand;

said cuff has a cincture joined thereto for clasping said cuff fast to such a forearm;

said element has a cincture joined thereto for clasping said element fast to the dorsal side of such a hand;

said cuff and said element cooperatively define means for non-contactingly bridging across a wrist, between such forearm and such hand, with said limb, to isolate said wrist and immobilizing such wrist; and said limb is unyieldably rigid.

2. A non-compressive wrist brace, according to claim 1, wherein:

said limb, cuff, and element comprise a one-piece unit.

3. A non-compressive wrist brace, according to claim 2, wherein:

said limb, cuff and element are formed of a common flexible material; and said limb has means formed therein rendering said limb inflexibly rigid.

4. A non-compressive wrist brace, according to claim 3, wherein:

said means formed in said limb comprises a spine shaped ridge.

5. A non-compressive wrist brace, according to claim 1, wherein:

said cincture joined to said cuff comprises means for compressively clasping only said dorsal side and said lateral flanks of said forearm.

6. A non-compressive wrist brace, comprising:

a body;

said body having (a) a limb, (b) first means for engaging only the dorsal side, and the lateral flanks, of a forearm, and (c) second means for engaging the dorsal side of a hand; and including only one pair of cinctures for clasping said first and second engaging means fast to such forearm and such hand, respectively; wherein said first and second engaging means, cooperatively with said limb, define means for non-contactingly bridging across a wrist, between such forearm and such hand, to isolate said wrist and immobilize the latter; and said limb is unyieldably rigid.

7. A non-compressive wrist brace, according to claim 6, wherein:

one cincture of said pair thereof comprises means for compressively clasping only said dorsal side and said lateral flanks of said forearm.

* * * * *